United States Patent [19]

Redmore

[11] 4,420,399

[45] Dec. 13, 1983

[54] QUATERNARY AMINOMETHYL PHOSPHONATES AS SCALE INHIBITORS

[75] Inventor: Derek Redmore, Webster Groves, MO

[73] Assignee: Petrolite Corporation, St. Louis, Mo.

[21] Appl. No.: 382,870

[22] Filed: May 28, 1982

Related U.S. Application Data

[63] Continuation-in-part of Ser. No. 898,250, Apr. 20, 1978, abandoned, Continuation of Ser. No. 409,875, Oct. 26, 1973, abandoned.

[51] Int. Cl.³ .............................................. C02F 5/14
[52] U.S. Cl. .................................. 210/700; 252/180
[58] Field of Search ............... 210/699, 700; 252/180, 252/181; 260/945

[56] References Cited

U.S. PATENT DOCUMENTS

| | | | |
|---|---|---|---|
| 2,635,112 | 4/1953 | Fields | 260/945 |
| 2,847,442 | 8/1958 | Sallman | 260/945 |
| 3,454,677 | 7/1969 | Burpitt | 260/945 |
| 3,536,752 | 10/1970 | Crutchfield | 260/945 |
| 3,966,630 | 6/1976 | Quinlan | 210/700 X |
| 4,330,487 | 5/1982 | Redmore et al. | 210/700 X |

*Primary Examiner*—Thomas G. Wyse
*Attorney, Agent, or Firm*—Sidney B. Ring; Leon Zitver

[57] ABSTRACT

This invention relates to quaternary aminomethyl phosphonates and uses thereof for example as scale inhibitors, corrosion inhibitors, chelating agents, etc.

12 Claims, No Drawings

QUATERNARY AMINOMETHYL PHOSPHONATES AS SCALE INHIBITORS

This application is a continuation-in-part of co-pending Application Ser. No. 898,250 filed Apr. 20, 1978, abandoned, which is a continuation of Ser. No. 409,875 filed Oct. 26, 1973, abandoned.

This invention relates to quaternary aminomethyl phosphonates for example of the idealized formula

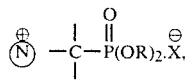

where (N) represents a quaternary amino moiety, R is hydrogen, an alcohol or a phenolic moiety, and X is an anion.

Specific general compounds include those of the following formula

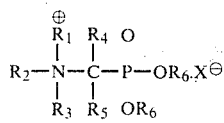

where $R_1$, $R_2$, $R_3$ are alkyl, alkenyl, aryl, cycloalkyl,

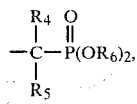

heterocyclic, etc., $R_4$ and $R_5$ are hydrogen or alkyl, and $R_6$ is an alcohol moiety such as alkyl, alkenyl, aryl, cycloalkyl, etc.

In addition, two of groups $R_1$, $R_2$, $R_3$ may be joined in a ring structure so that the amino group is part of the ring, for example

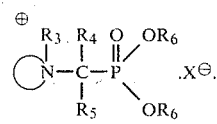

In addition, in the case of a polyamine compound, two amino groups may be joined for example

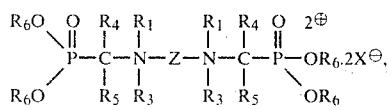

where Z is a linking group, for example alkylene, etc.

In addition, the two amino group may be part of the ring, for example

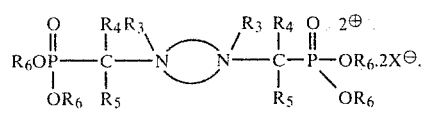

The products are prepared by the following reaction sequence:

Step 1.

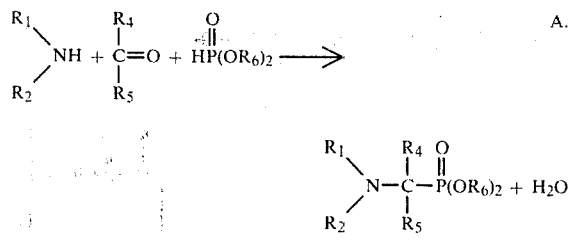

Step 2.

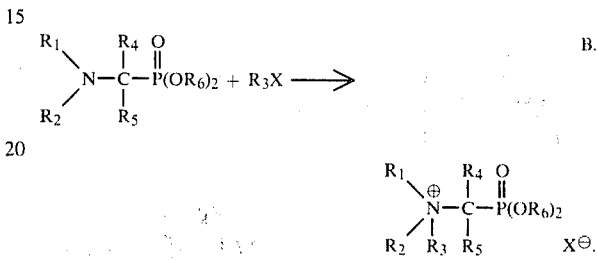

Step 1 is a well known reaction and is described for example by Fields, J. Amer. Chem. Soc., Vol. 74, 1528 (1952). The carbonyl compound preferred in this step is formaldehyde ($R_4$, $R_5$=H). The amine can be aliphatic, e.g., $R_1$, $R_2$=$CH_3$, $C_2H_5$, $C_3H_7$, $C_4H_9$, $C_5H_{11}$, $C_6H_{12}$, etc., or cyclic, e.g., morpholine, piperidine, pyrrolidine, thiomorpholine, etc., a polyamine, etc.

This invention relates to quaternary aminophosphonates having the general formula

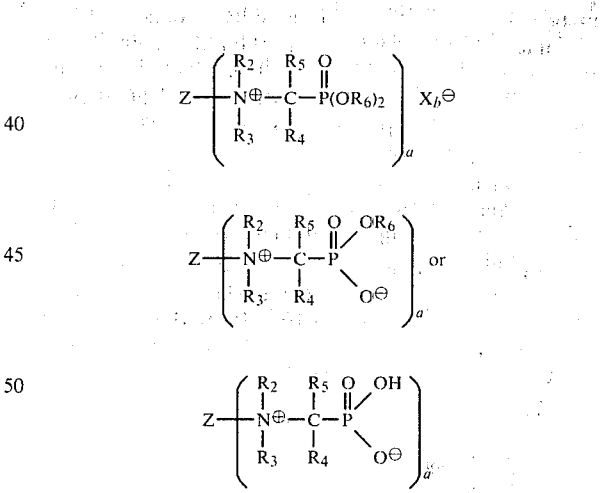

where Z is alkylene, alkyl, alkenyl, aryl or aralkyl, $R_2$ and $R_3$ are alkyl, alkenyl, aryl, or aralkyl, $R_4$ and $R_5$ are hydrogen or alkyl, $R_6$ is alkyl having 1 to 4 carbon atoms, a is 1 or 2 and b is 1 or 2, with the proviso that when Z is alkylene, a and b are 2 and when Z is alkyl, alkenyl, aryl or aralkyl a and b are 1, with the further proviso that Z and $R_2$ may be joined to form a cyclic group and X is an anion.

Also included within the scope of this invention is the product formed where a primary rather than a secondary amine is reacted. Thus, Step 1 can be expressed by the following equation:

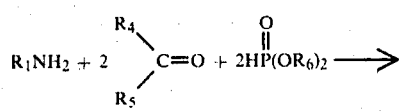

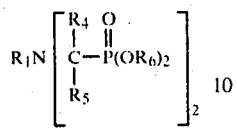

and Step 2 becomes:

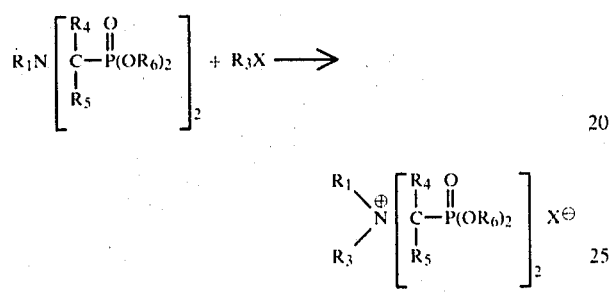

Step 2. This step is conveniently carried out by heating the α-aminophosphonate of step 1 with an alkylating reagent $R_3X$ is an inert solvent such as dioxan, ether, methylene chloride, chloroform, alcohols, e.g., methanol, ethanol, butanol, etc. The alkylating reagents which can be used include dialkylsulfates such as dimethyl sulfate, diethyl sulfate, etc., alkyl halides such as methyl iodide, methyl chloride, ethyl bromide, propyl bromide, dodecyl bromide, benzyl chloride, and highly reactive alkylating reagents such as tri-alkyl oxonium fluoroborates such as triethyloxonium or trimethyloxonium tetrafluoroborate, corresponding oxonium hexafluorophosphates, etc.

In order to obtain pure products according to step 2 it is necessary to use an alkylating reagent in which the anion $X^\ominus$ formed in the alkylation process has low nucleophilicity. Thus dimethyl or diethyl sulfate are particularly useful alkylating reagents as are reagents such as triethyloxonium tetrafluoroborate. In cases where $X^\ominus$ is a nucleophilic anion the product of step 2 can react further as shown below:

Step 3.

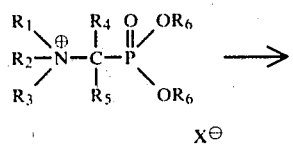

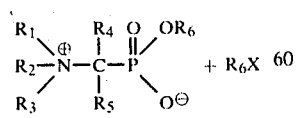

The alkylating reagent $R_6X$ can then compete with $R_3X$ in step 2 so that a typical alkylating reaction with an alkylbromide (bromide is moderately nucleophilic) can yield a mixture consisting of quaternary B and betaine C, e.g.,

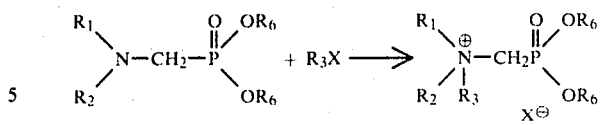

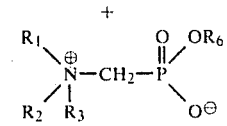

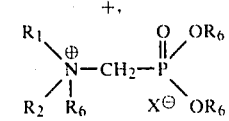

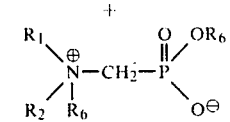

With appropriate reagents the conversion of A to C can be an isomerization process catalyzed by $R_3X$.

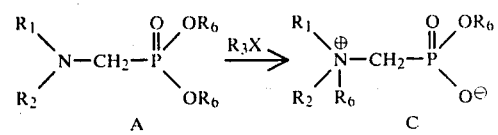

The quaternary B in which $X^\ominus$ is a non-nucleophilic anion can be converted into betaine C by addition of a nucleophile such as sodium iodide.

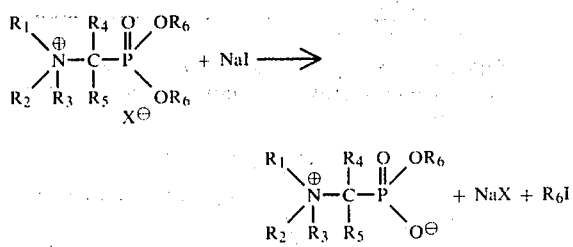

The following examples are presented by way of illustration and not of limitation.

EXAMPLE 1

Diethyl N,N-dibutylamino methyl phosphonate

To a stirred mixture of dibutylamine (65 g:0.5 mole) and diethyl phosphite (69 g:0.5 mole) was added 37% aqueous formaldehyde (41 g:0.5 mole) during 50 min. The reaction temperature rose to 75° rapidly and was maintained at 70°-75° by intermittent cooling. The water was removed under vacuum after completion of the addition. Distillation of the residue gave pure diethyl N,N-dibutylamino methyl phosphonate; 120 g (85%) bp. 100°-103°/0.1 mm. Anal. Calcd. N,50.2%, P, 11.11%. Found N, 4.86%, P, 11.53%.

The structure of the product is

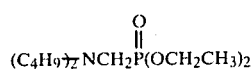

EXAMPLE 2

To a stirred mixture of morpholine (43.5 g:0.5 mole) and diethyl phosphite (69 g:0.5 mole) was added aqueous formaldehyde (41 g:0.5 mole) during 60 min. at 50°–60°. After stirring for an additional 1 hr. water was removed in vacuo and the resulting oil distilled. Pure diethyl morpholinomethylphosphonate, 105 g (87%) bp 108°–9°/0.1 mm was obtained.

Analysis, calcd. N, 5.90%, P, 13.08; Found N, 5.94%, P, 13.39%.

Product is

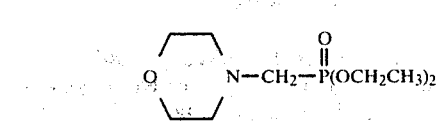

To avoid repetition the following table summarizes preparations of further α-amino methyl phosphonates by the procedures of Examples 1 and 2.

Preparations of $$R_1 \diagdown N-CH_2-P(-OR_3)_2 \atop R_2 \diagup \qquad \| \atop O$$

| | $R_1$ | $R_2$ | $R_3$ | Yield |
|---|---|---|---|---|
| Example 3 | n-C$_4$H$_9$ | n-C$_4$H$_9$ | C$_4$H$_9$ | 87% |
| Example 4 | Ph—CH$_2$ | CH$_3$ | C$_2$H$_5$ | 53% |
| Example 5 | (CH$_2$)$_5$ | | C$_2$H$_5$ | 90% |
| Example 6 | (CH$_2$)$_5$ | | C$_4$H$_9$ | 85% |
| Example 7 | (CH$_2$)$_5$ | | CH$_3$ | 75% |
| Example 8 | (CH$_3$)$_2$CH | (CH$_3$)$_2$CH | C$_2$H$_5$ | 46% |
| Example 9 | C$_2$H$_5$ | C$_2$H$_5$ | C$_2$H$_5$ | 87% |
| Example 10 | n-C$_3$H$_7$ | n-C$_3$H$_7$ | C$_2$H$_5$ | 91% |

The following examples illustrate quaternization reactions of α-aminomethylphosphonates described in Examples 1–10.

EXAMPLE 11

To the α-aminomethylphosphonate of Example 1 (20 g:0.072 mole) dissolved in dioxane (40 ml) was added dimethyl sulfate (9.05 g:0.072 mole) dropwise in 10 min. A slight exotherm was noted. After stirring at ambient temperature for 4 hr. evaporation of the solvent yielded the quaternary as a viscous gum. The structure is represented by formula:

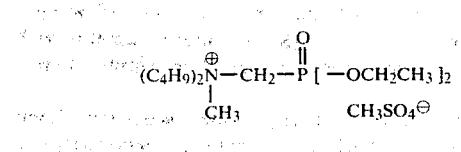

EXAMPLE 12

To the piperodinomethylphosphonate of Example 5 (4.7 g; 0.02 mole) in methylene chloride (30 ml) cooled to 5° was added a 1 Molar solution of triethyloxonium tetrafluoroborate (20 ml; 0.02 mole) in 10 min. After stirring at room temperature for 1 hr. evaporation of the solvent yielded pure quaternary. Infrared showed P=O at 8.05μ and broad absorption between 9.3 and 9.9μ for P—O—C and BF$_4$⊖. NMR in CDCl$_3$ showed δ1.36 (CH$_3$—), 1.7–2.1 (CH$_2$ piperidine ring), 3.2–4.0 (CH$_2$—N⊕) and 4.30 (OCH$_2$).

The structure is

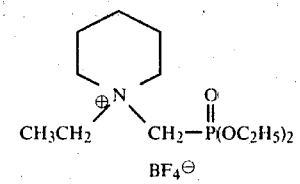

EXAMPLE 13

To the phosphonate of Example 4 (30 g; 0.11 mole) in dioxane (50 ml) was added dimethyl sulfate (14 g; 0.11 mole) in 5 mins. The reaction temperature rose to 50° and gradually returned to room temperature during 3 hrs. stirring. Evaporation of the solvent yielded the quaternary of structure:

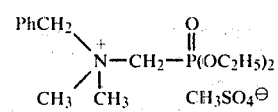

EXAMPLE 14

To the aminomethylphosphonate of Example 5 (47 g; 0.2 mole) dissolved in ethanol (60 ml) was added benzyl bromide (34.3; 0.2 mole). The mixture was heated to gentle reflux whereupon gas evolution was noted. Solvent was removed in vacuo to yield a viscous water soluble gum.

NMr spectrum showed δ1.32 (CH$_3$), 1.7–2.3 (ring CH$_2$), 3.3–4.6 (OC$\underline{H}_2$, N⊕C$\underline{H}_2$), 5.0 (PhC$\underline{H}_2$N⊕), 7.3–7.9 (Ph$\underline{H}$).

Bromine content 9.8%.

These data are consistent with the product being a mixture of

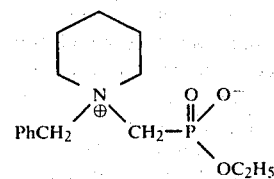 and

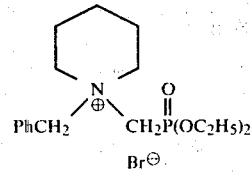

To avoid further repetition of details the following table summarizes additional preparations of quaternary compounds.

| Example | Method | Quaternary Reagent | Aminophosphonate Reacted |
|---|---|---|---|
| Example 15 | as Ex. 11 | (C$_2$H$_5$)$_2$SO$_4$ | Example 1 |
| Example 16 | as Ex. 11 | (C$_2$H$_5$)$_2$SO$_4$ | Example 3 |
| Example 17 | as Ex. 12 | (C$_2$H$_5$)$_3$O$^+$BF$_4$$^-$ | Example 2 |
| Example 18 | as Ex. 12 | (C$_2$H$_5$)$_3$O$^+$PF$_6$$^-$ | Example 2 |
| Example 19 | as Ex. 11 | (CH$_3$)$_2$SO$_4$ | Example 2 |
| Example 20 | as Ex. 11 | (CH$_3$)$_2$SO$_4$ | Example 5 |

| Example | Method | Quaternary Reagent | Aminophosphonate Reacted |
|---|---|---|---|
| Example 21 | as Ex. 11 | $(CH_3)_2SO_4$ | Example 6 |
| Example 22 | as Ex. 11 | $(CH_3)_2SO_4$ | Example 8 |
| Example 23 | as Ex. 11 | $(CH_3)_2SO_4$ | Example 10 |
| Example 24 | as Ex. 11 | $(C_2H_5)_2SO_4$ | Example 10 |
| Example 25 | as Ex. 14 | $CH_3I$ | Example 2 |

The quaternary compounds of Examples 11–24 can be hydrolyzed in the normal manner to yield phosphonic acid molecules of the general formula:

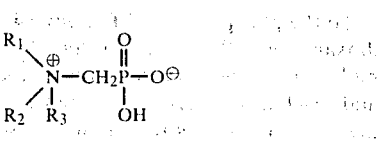

EXAMPLE 26

The quaternary phosphonate of Example 19 (8 g) was heated under reflux in 18% HCl (75 ml) for 12 hrs. The aqueous acid was removed under vacuum and the crude gum purified by dissolution in ethanol and precipitation with ether. This dissolution-precipitation sequence was repeated 3 times.

NMR in $D_2O$ showed peaks at $\delta 3.52$ ($N^{\oplus}CH_3$), 3.85 and 4.13 ($OCH_2$ and $N^{\oplus}CH_2$).

Analysis Calculated for $C_6H_{14}NO_4P$. N, 7.18%, P, 15.9%. Equivalent weight 195. Found N, 6.7%, P, 16.7%. Equivalent weight 201.

These date are consistent with the structure:

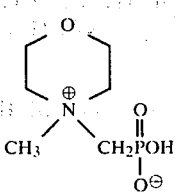

The following are non-limiting examples of amines that can be employed to yield compounds of this invention.

I. MONOAMINES

A. Primary monoamines.—These include compounds of the formula $R-NH_2$, where R is a substituted group preferably a hydrocarbon group, for example alkyl, cycloalkyl, aryl, alkenyl, heterocyclic, substituted derivatives of the above, etc.

Alkyl

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, eicosyl, docosyl, etc. having 1–50 or more carbons, such as 1–30, but preferably 1–18 carbons.

The term "alkyl" also includes isomers of the straight chain group wherein branching occurs along the chain, for example

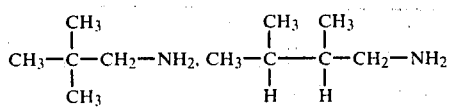

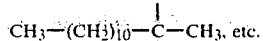

Alkenyl and Alkinyl

These include unsaturated analogues of alkyl groups containing one or more

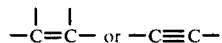

groups, for example decenyl, dodecenyl, tridecenyl, tetradecenyl, pentadecenyl, hexadecyl, heptadecenyl, octadecenyl, etc., dienes for example octadienyl, etc. trienes, for example octatrienyl, etc., alkinyl, for example butinyl, etc.

Cycloalkyl

These include

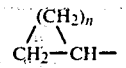

for example cyclobutyl, cyclopentyl, cyclohexyl, cycloheptyl, cyclooctyl, etc.; substituted derivatives thereof, for example alkyl or polyalkyl, for example alkyl cyclohexyl, dialkyl cyclohexyl, etc.

Heterocyclic

These include furyl, pyranyl, hydrogenated furyl, pyranyl, etc. groups.

B. Secondary amines.—These include amines of the formula

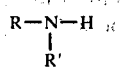

where R and R', which may or may not be the same, have the same meaning as stated above, for example dimethyl amine, diethyl amine, dipropyl amine, diamylamine, dihexyl amine, dioctyl amine, didodecyl amine, dihexyldecyl amine, etc., methyl ethyl amine, methyl octyl amine, butyl octylamine, methyl octadecyl amine, etc.; methyl octadecenyl amine, dioctadecenyl amine, etc.; dicyclohexyl amine, methyl cyclohexyl amine, etc.; methyl furyl amine, methyl benzyl amine.

C. Commercial amines.—Representative commercial amines are available, for example, these shown in the following tables.

The nomenclature of these amines is derived from either their chain length or source of raw materials, for example, Armeen 8D—octyl amine
Armeen C—coconut oil amine
Armeen S—soybean oil amine
Armeen T—tallow amine
Armeen O—oleyl amine
Armeen HT—hydrogenated tallow amine
Armeen DMCD—dihydrogenated tallow amine
Armeen M2HT—dimethyl coconut oil amine.

Products with "D" designate distilled grade. Products without "D" designate technical grade.

Other commercial amines include the following:

"Primene" amines $$CH_3-\underset{\underset{CH_3}{|}}{\overset{\overset{CH_3}{|}}{C}}-\left(CH_2-\underset{\underset{CH_3}{|}}{\overset{\overset{CH_3}{|}}{C}}\right)_n-NH_2$$

Rosin Amine D

[Structure of Rosin Amine D: a tricyclic decahydrophenanthrene skeleton with H₂NCH₂ and CH₃ substituents on one ring carbon, CH₃ on the ring junction, and a CH(CH₃)₂ isopropyl group]

D. Cyclic secondary amines.—Also included within the definition of secondary are those amines where two of the R groups are joined in a cyclic structure such as $$HN\begin{matrix}\diagup R\!-\!\!\!\!-\!\!\!\!-\!\!\!\!\raisebox{0pt}{\rule{0pt}{0pt}}\\ \diagdown R'\!-\!\!\!\!-\!\!\!\!-\!\!\!\!\raisebox{0pt}{\rule{0pt}{0pt}}\end{matrix}$$

Examples of these amines also include piperidine, morpholine, pyrrolidine, etc.

$$\begin{matrix}R-CH-\overset{O}{\underset{\|}{C}}\\ \phantom{xxxx}\diagdown\\ \phantom{xxxxxxx}N-CH_2CH_2NH_2\\ \phantom{xxxx}\diagup\\ R'-CH-\underset{\|}{\overset{\phantom{\|}}{C}}\\ \phantom{xxxx}O\end{matrix}$$

(R and R'=alkyl, alkenyl, hydrogen, etc.), etc.

II. POLYAMINES

These include polyamines corresponding to the formula $$\begin{matrix}R''\\ \diagdown\\ \phantom{x}N-R'-(NR')_x-N\\ \diagup\phantom{xxxxxxxxxxxxx}\diagdown\\ R''\phantom{xxxxxxxxxxxxxxxx}R''\end{matrix}$$

x = 0 to 8 in which R" (which may or may not be the same) is hydrogen, alkyl, cycloalkyl, aryl, or aralkyl and R' is a divalent radical such as $$-CH_2CH_2-,\ -CH_2CH_2CH_2-,\ -\underset{\underset{CH_3}{|}}{\overset{\overset{H}{|}}{C}}-CH_2$$

$$-CH_2CH-CH_2-,\ -CH-CH-,\ -CH-CH-CH-\\ \phantom{xxx}|\phantom{xxxxxxxxxx}|\phantom{xx}|\phantom{xxxxxx}|\phantom{xx}|\phantom{xx}|\\ \phantom{xxx}CH_3\phantom{xxxxxxxxx}CH_3\ CH_3\phantom{xxx}CH_3\ CH_3\ CH_3$$

etc.

Ethylenediamine
Diethylenetriamine
Triethylenetetramine
Tetraethylenepentamine
Propylenediamine
Dipropylenetriamine
Tripropylenetetramine
Butylenediamine
Aminoethylpropylenediamine
Aminoethylbutylenediamine $$C_{17}H_{33}-\overset{H}{\underset{}{N}}-C_3H_6-NH_2$$

Other polyamines in which the nitrogen atoms are separated by a carbon chain having 4 or more carbon atoms include the following: pentamethylenediamine, and especially hexamethylenediamine.

Another class of polyamines which may be employed are those sold under the trademark "Duomeen" which is a designation for certain diamines. "Duomeen" amines have the following general formula:

$$R-\overset{H}{\underset{}{N}}-CH_2-CH_2-CH_2-NH_2$$

R is an alkyl group derived from a fatty acid or from the mixed fatty acids as obtained from certain oils. The specific "Duomeen" and the source of the radical R are as follows:

(1) "Duomeen" 12, R = lauric
(2) "Duomeen" C, R = coconut oil fatty acid
(3) Similarly, a comparable diamine, obtained from Rosin Amine D and acrylonitrile, can be prepared.

[Structure: Rosin Amine D derivative with CH₂NH—CH₂CH₂CH₂NH₂ substituent]

Additional examples of polyamines include the following:

$$C_8H_{17}-\overset{H}{\underset{}{N}}-CH_2CH_2-NH_2$$
N—octyl ethylenediamine $$C_{14}H_{29}-\overset{H}{\underset{}{N}}-CH_2CH_2-NH_2$$
N—tetradecyl ethylenediamine $$C_{16}H_{33}-\overset{H}{\underset{}{N}}-CH_2-CH_2-CH_2-NH_2$$
N—hexadecylethylenediamine $$C_{12}H_{25}-\overset{H}{\underset{}{N}}-C_2H_4-\overset{H}{\underset{}{N}}-C_2H_4-\overset{H}{\underset{}{N}}-C_2H_4-NH_2$$
N—dodecyl triethylenetetramine $$C_{12}H_{25}-\overset{H}{\underset{}{N}}-C_3H_6-NH_2$$
N—dodecyl propylenediamine Diamines containing tertiary amino groups for example

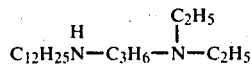

It is to be noted that the above examples show high molal groups, i.e., 8 carbon atoms or more. The same derivatives in which methyl, ethyl, propyl, butyl, amyl, hexyl groups, or the like, appear instead of octyl, decyl, etc., are equally satisfactory.

Acylated polyamines can also be employed provided they are sufficiently basic to form salts, for example:

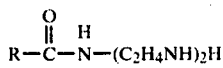

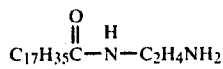

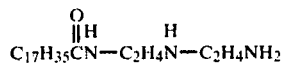

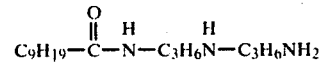

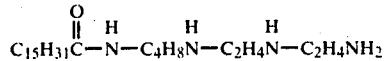

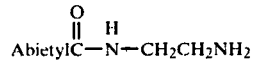

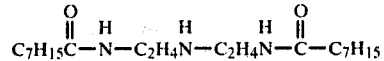

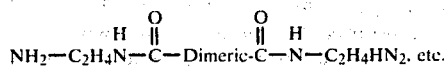

Any hydrocarbon halide, e.g., alkyl, alkenyl, cycloalkenyl, aralkyl, etc., halide which contains at least one carbon atom and up to about thirty carbon atoms or more per molecule can be employed to quaternize the amines of this invention. It is especially preferred to use alkyl halides having between about one to about eighteen carbon atoms per molecule. The halogen portion of the alkyl halide reactant molecule can be any halogen atom, i.e., chlorine, bromine, fluorine, and iodine. In practice, the alkyl bromides and chlorides are used, due to their greater commercial availability. Non-limiting examples of the alkyl halide reactant are methyl chloride; ethyl chloride; propyl chloride; n-butyl chloride; sec-butyl iodide; n-amyl bromide; isoamyl chloride; n-hexyl bromide; n-hexyl iodide; 2-ethyl-hexyl chloride; n-octyl bromide; decyl iodide; dodecyl bromide; 7-ethyl-2-methyl-undecyl iodide; tetradecyl bromide; hexadecyl bromide; octadecyl bromide; tetracosyl iodide; hexacosyl bromide. In addition, alkenyl halides can also be employed, for example, the alkenyl halides corresponding to the above examples.

USE AS SCALE INHIBITORS

Most commercial water contains alkaline earth metal cations, such as calcium, barium, magnesium, etc., and anions such as bicarbonate, carbonate, sulfate, oxalate, phosphate, silicate, fluoride, etc. When combinations of these anions and cations are present in concentrations which exceed the solubility of their reaction products, precipitates form until their product solubility concentrations are no longer exceeded. For example, when the concentrations of calcium ion and carbonate ion exceed the solubility of the calcium carbonate reaction product, a solid phase of calcium carbonate will form as a precipitate.

Solubility product concentrations are exceeded for various reasons, such as evaporation of the water phase, change in pH, pressure or temperature, and the introduction of additional ions which can form insoluble compounds with the ions already present in the solution.

As these reaction products precipitate on the surfaces of the water-carrying system, they form scale. The scale prevents effective heat transfer, interferes with fluid flow, facilitates corrosive processes, and harbors bacteria. Scale is an expensive problem in many industrial water systems, causing delays and shutdowns for cleaning and removal.

Scale-forming compounds can be prevented from precipitating by inactivating their cations with chelating of sequestering agents, so that the solubility of their reaction products is not exceeded. Generally, this approach requires many times as much chelating or sequestering agent as cation present, and the use of large amounts of treating agent is seldom desirable or economical.

More than twenty-five years ago it was discovered that certain inorganic polyphosphates would prevent such precipitation when added in amounts far less than the concentrations needed for sequestering or chelating. See, for example, Hatch and Rice, "Industrial Engineering Chemistry," vol. 31, p. 51, at 53; Reitemeier and Buchrer, "Journal of Physical Chemistry," vol. 44, No. 5, p. 535 at 536 (May 1940); Fink and Richardson U.S. Pat. No. 2,358,222; and Hatch U.S. Pat. No. 2,539,305. When a precipitation inhibitor is present in a potentially scale-forming system at a markedly lower concentration than that required for sequestering the scale forming cation, it is said to be present in "threshold" amounts. Generally, sequestering takes place at a weight ratio of threshold active compound to scale-forming cation component of greater than about ten to one, and threshold inhibition generally takes place at a weight ratio of threshold active compound to scale-forming cation component of less than about 0.5 to 1.

The "threshold" concentration range can be demonstrated in the following manner. When a typical scale-forming solution containing the cation of a relatively insoluble compound and a very small amount of a threshold active inhibitor, the relatively insoluble compound will not precipitate even when its normal equilibrium concentration has been exceeded. If more of the threshold active compound is added, a concentration is reached where turbidity or a precipitate of uncertain composition results. As still more of the threshold active compound is added, the solution again becomes clear. This is due to the fact that threshold active compounds in high concentrations also act as sequestering agents, although sequestering agents are not necessarily "threshold" compounds. Thus, there is an intermediate zone between the high concentrations at which they act as threshold inhibitors. Therefore, one could also define "threshold" concentrations as all concentrations of threshold active compounds below that concentration at which this turbid zone or precipitate is formed. Generally the threshold active compound will be used in a weight ratio of the compound to the cation component of the scale-forming salts which does not exceed about 1.

The polyphosphates are generally effective threshold inhibitors for many scale-forming compounds at temperatures below 100° F. But after prolonged periods at higher temperatures, they lose some of their effectiveness. Moreover, in an acid solution, they revert to ineffective or less effective compounds.

A compound that has sequestering powers does not predictably have threshold inhibiting properties. For example, ethylenediamine tetracetic acid salts are powerful sequesterants but have no threshold activities.

I have now discovered a process for inhibiting scale such as calcium, barium and magnesium carbonate, sulfate, silicate, etc., scale which comprises employing threshold amounts of the compositions of this invention.

Scale formation from aqueous solutions containing an oxide variety of scale forming compounds, such as calcium, barium and magnesium carbonate, sulfate, silicate, oxalates, phosphates, hydroxides, fluorides and the like are inhibited by the use of threshold amounts of the compositions of this invention which are effective in small amounts, such as less than 100 ppm and are preferably used in concentrations of less than 25 ppm.

The scale inhibitors of the present invention illustrate improved inhibiting effect at high temperatures when compared to prior art compounds. The compounds of the present invention will inhibit the deposition of scale-forming alkaline earth metal compounds on a surface in contact with aqueous solution of the alkaline earth metal compounds over a wide temperature range. Generally, the temperatures of the aqueous solution will be at least 40° F., although significantly lower temperatures will often be encountered. The preferred temperature range for inhibition of scale deposition is from about 130° to about 350° F. The aqueous solutions or brines requiring treatment generally contain about 50 ppm to about 50,000 ppm of scale-forming salts. The compounds of the present invention effectively inhibit scale formation when present in an amount of from 0.1 to about 100 ppm, and preferably 0.2 to 25 ppm wherein the amounts of the inhibitor are based upon the total aqueous system. There does not appear to be a concentration below which the compounds of the present invention are totally ineffective. A very small amount of the scale inhibitor is effective to a correspondingly limited degree, and the threshold effect is obtained with less than 0.1 ppm. There is no reason to believe that this is the minimum effective concentration. The scale inhibitors of the present invention are effective in both brine, such as sea water, and acid solutions.

These methylene phosphonates are threshold active scale inhibitors at room temperature, and are also effective at elevated temperatures. They also retain their effectiveness in acid and salt solution and have excellent solubility in waters with high hardness content.

Calcium Scale Inhibition Test

The procedure utilized to determine the effectiveness of my scale inhibitors in regard to calcium scale is as follows:

Several 50 ml. samples of a 0.04 sodium bicarbonate solution are placed in 100 ml. bottles. To these solutions is added the inhibitor in various known concentrations. 50 ml. samples of a 0.02 M $CaCl_2$ solution are then added.

A total hardness determination is then made on the 50-50 mixture utilizing the well known Schwarzenbach titration. The samples are placed in a water bath and heated at 180° F. 10 ml. samples are taken from each bottle at 2 and 4 hour periods. These samples are filtered through millipore filters and the total hardness of the filtrates are determined by titration.

$$\frac{\text{Total hardness after heating}}{\text{Total hardness before heating}} \times 100 = \% \text{ inhibition}$$

Inhibition against $CaCO_3$ precipitation

| Compound | Concentration | % Inhibition at 2 hrs. | % Inhibition at 4 hrs. |
|---|---|---|---|
| Example 11 | 10 ppm | 40% | 35% |
| Example 12 | 50 ppm | 48% | 44% |
| Example 19 | 50 ppm | 45% | 42% |
| Example 26 | 10 ppm | 43% | 41% |
| Example 26 | 50 ppm | 51% | 48% |
| Commercial Phosphonate | 50 ppm | 42% | 36% |

Barium Sulfate Inhibition

A simple visual comparison test was used to demonstrate inhibition of precipitation of Barium sulfate in the following manner:

Test solutions were prepared as follows:
A. Containing barium ion:
  560 mg/liter $BaCl_2.2H_2O$
  30 g/liter NaCl
B. Containing sulfate ion:
  800 mg/liter $Na_2SO_4$
  30 g/liter NaCl To 50 ml of solution A (containing $Ba^{++}$) was added inhibitor followed by 50 ml of solution B (containing $SO_4^{--}$) with good mixing. A visual grading was made on a scale 0 no precipitation to 5, blank with no inhibitor. The table below shows effectiveness.

| Compound | Concentration | Rating at 4 hrs. | Rating at 24 hrs. |
|---|---|---|---|
| Example 11 | 30 ppm | 1 | 1 |
| Example 13 | 15 ppm | 2 | 3 |
| Example 19 | 15 ppm | 2 | 2 |
| Example 19 | 50 ppm | 1 | 1 |
| Blank | — | 5 | 5 |
| Commercial phosphonate A | 15 ppm | 5 | 5 |
| Commercial phosphonate B | 20 ppm | 2 | 3 |
|  | 20 ppm | 2 | 3 |
| Phosphate | 15 ppm | 1.5 | 2 |

The compositions of this invention are also useful as corrosion inhibitors, flocculants, biocides, fuel additives, etc.

I claim:

1. A process of inhibiting scale which comprises treating an aqueous system with scale inhibiting amounts of a quaternary aminophosphonate having the general formula

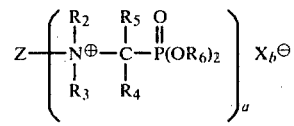

$$Z+\begin{pmatrix} R_2 & R_5 & O & OR_6 \\ | & | & || & / \\ N^\oplus-C-P \\ | & | & \\ R_3 & R_4 & O^\ominus \end{pmatrix}_a \text{ or}$$

$$Z+\begin{pmatrix} R_2 & R_5 & O & OH \\ | & | & || & / \\ N^\oplus-C-P \\ | & | & \\ R_3 & R_4 & O^\ominus \end{pmatrix}_a$$

where Z is alkylene, alkyl, alkenyl, aryl or aralkyl, $R_2$ and $R_3$ are alkyl, alkenyl, aryl, or aralkyl, $R_4$ and $R_5$ are hydrogen or alkyl, $R_6$ is alkyl having 1 to 4 carbon atoms, a is 1 or 2 and b is 1 or 2, with the proviso that when Z is alkylene, a and b are 2 and when Z is alkyl, alkenyl, aryl or aralkyl a and b are 1, with the further proviso that Z and $R_2$ may be joined to form a cyclic group and X is an anion.

2. The process of claim 1 where the quaternary aminophosphonate has the general formula $$\begin{array}{c} R_1 \setminus \quad R_3 \quad O \\ \quad \diagdown | \quad || \\ \quad N^\oplus-CH_2-P(OR_6)_2.X^\ominus \\ \diagup \\ R_2 \end{array}$$

where $R_1$, $R_2$ and $R_3$ are alkyl, alkenyl, aryl, aralkyl, or $R_1$ and $R_2$ may be joined to form a cyclic group and X is an anion.

3. The process of claim 2 where $R_1$ and $R_2$ are joined as an alkylene group.

4. The process of claim 2 where $R_1$ and $R_2$ are joined as an alkylene ether group.

5. The process of claim 2 where $R_1$ and $R_2$ are joined as an alkyleneamino group.

6. The process of claim 2 where the quaternary has the formula $$\begin{array}{c} \diagup\diagdown CH_2CH_3 \quad O \\ \quad | \quad || \\ \oplus N-CH_2-P(OC_2H_5)_2-BF_4^\ominus. \\ \diagdown\diagup \end{array}$$

7. The process of claim 2 where the quaternary aminophosphate is present in an amount of from about 0.1 to about 100 ppm of the total aqueous system.

8. The process of claim 2 where the quaternary compound has the formula $$\begin{array}{c} PhCH_2 \quad CH_3 \quad O \\ \diagdown | \quad || \\ N^\oplus-CH_2-P(OC_2H_5)_2.CH_3SO_4^\ominus \\ \diagup \\ CH_3 \end{array}$$

where Ph is phenyl.

9. The process of claim 2 where the quaternary compound has the formula $$\begin{array}{c} \diagup\diagdown CH_3 \quad O \\ \quad | \quad || \\ O \quad \oplus N-CH_2-P(OC_2H_5)_2.CH_3SO_4^\ominus. \\ \diagdown\diagup \end{array}$$

10. The process of claim 1 where the quaternary compound has the formula $$\begin{array}{c} \diagup\diagdown CH_3 \quad O \quad OH \\ \quad | \quad ||\diagup \\ O \quad \oplus N-CH_2P \\ \diagdown\diagup \quad \diagdown O^\ominus \end{array}$$

11. The process of claim 1 where the quaternary has the formula $$\begin{array}{c} \quad\quad\quad\quad\quad\quad\quad\quad 2\oplus \\ R_6O \quad O \quad R_4 \quad R_2 \quad R_2 \quad R_4 \quad O \quad OR_6 \\ \diagdown || \quad | \quad | \quad | \quad | \quad || \diagup \\ P-C-N-Z-N-C-P \quad .2X^\ominus \\ \diagup \quad | \quad | \quad | \quad | \quad \diagdown \\ R_6O \quad R_5 \quad R_3 \quad R_3 \quad R_5 \quad OR_6 \end{array}$$

where Z is alkylene and where $R_2$, $R_3$, $R_4$, $R_5$, $R_6$ and X have the same meaning as in claim 1.

12. The process of claim 1 where the quaternary aminophosphonate is present in an amount of from about 0.1 to about 100 ppm of the total aqueous system.

* * * * *